United States Patent [19]

Jernigan

[11] Patent Number: 5,434,055
[45] Date of Patent: Jul. 18, 1995

[54] COMPOSITIONS USEFUL IN ANAEROBIC DETERMINATION OF ANALYTES

[75] Inventor: Walter Jernigan, Indianapolis, Ind.

[73] Assignee: Boehringer Mannheim Corporation, Indianapolis, Ind.

[21] Appl. No.: 239,025

[22] Filed: May 6, 1994

Related U.S. Application Data

[62] Division of Ser. No. 10,232, Jan. 28, 1993, abandoned.

[51] Int. Cl.⁶ .......................... C12Q 1/60; C12Q 1/54; C12Q 1/26; C12Q 1/00
[52] U.S. Cl. .......................... 435/11; 435/4; 435/25; 435/26; 435/14
[58] Field of Search ............... 435/11, 4, 25, 26, 14, 435/28

[56] References Cited

U.S. PATENT DOCUMENTS

| | | | |
|---|---|---|---|
| 4,576,913 | 3/1986 | Adachi et al. | 435/26 |
| 4,701,420 | 10/1987 | Thunberg et al. | 435/26 |
| 4,912,035 | 3/1990 | Belly et al. | 435/25 |
| 4,929,544 | 5/1990 | Freitag | 435/11 |
| 5,141,855 | 8/1992 | Schmittou | 435/25 |

OTHER PUBLICATIONS

Al–Jobore et al; Chem. Abstract 94(1): 1872p from Can. J. Biochem., 58(12), 1397–1404 (1980).

*Primary Examiner*—Michael G. Wityshyn
*Assistant Examiner*—Louise N. Leary
*Attorney, Agent, or Firm*—Felfe & Lynch

[57] ABSTRACT

The invention describes a composition useful in determining sample analytes, where the determination is carried out anaerobically. The compositions include an analyte oxidizing agent, an electron transfer agent, ferric ions, and two chelators. The first chelator complexes to ferric ions, but does not have good affinity for ferrous ions. The second chelator does chelate ferrous ions, and forms a colored complex with the ion. It is the colored complex which serves as the indicator for the analyte. Different formulations of the composition are described.

11 Claims, No Drawings

COMPOSITIONS USEFUL IN ANAEROBIC DETERMINATION OF ANALYTES

This application is a divisional of Ser. No. 08/010,232 filed Jan. 28, 1993, now abandoned.

FIELD OF THE INVENTION

This invention relates to compositions useful in determination of particular analytes. In particular, the invention relates to compositions where a ferrous ion containing complex is the end result of a series of reactions, where the amount of complex can be correlated to the amount of analyte in the sample.

BACKGROUND AND PRIOR ART

The central concern of clinical chemistry is the qualitative and quantitative determination of specific analytes in samples. Of special concern is the analysis of body fluid samples, such as blood, serum, urine, and so forth. Determination of the presence and/or amount of various analytes, followed by comparison to established parameters determines diagnosis of diseased or abnormal states.

The literature on analytical determination of body fluid samples is an enormous one, as the art has investigated the determination of, e.g., glucose, cholesterol, creatine, sarcosine, urea, and other substances in samples of blood, serum, urine, and so forth.

The early clinical literature taught various non-enzymometric methods for determining analytes. Exemplary of this are the early glucose determination tests taught by Kaplan and Pesce in Clinical Chemistry: Theory, Analysis and Correlation (Mosby, 1984), pages 1032-1042. Such tests include the reduction of copper ions, reaction of copper with molybdate, and so forth. As this reference points out, these methods are insufficiently accurate, due to poor specificity, and interference by other analytes. One method described by Kaplan, et al. is the alkaline ferricyanide test. This method involves heating a solution containing glucose in the presence of ferricyanide, under alkaline conditions. The reaction:

is accompanied by a change in color from yellow to colorless. Either this decrease in color is measured or the reaction of the colorless ferrocyanide ion with a ferric ion to form the intensely colored precipitate "Prussian Blue" is measured.

These early "chelation" type tests became replaced by more specific assays as enzymology became a more developed science. Enzymes are known for their extreme specificity, so via the use of an appropriate enzyme, the skilled artisan could determine, rather easily, whether or not a particular analyte is present, and how much. These enzymatic systems must be combined with indicator systems which, in combination with the enzyme reaction, form a detectable signal. Kaplan describes a glucose-hexokinase system, as well as a glucose oxidase system, and these are fairly well known to the art. They are used in connection with indicator systems such as the "coupled indicators" known as Trinder reagents, or oxidizable indicators such as o-tolidine and 3,3', 5,5'-tetramethylbenzidine. In such systems, reaction of the enzyme with its substrate yields a surplus of electrons carried by the enzyme, which are removed by the indicator systems. Color formation follows, indicating presence, absence, or amount of analyte in the sample.

The patent literature is replete with discussions of such systems. A by no means exhaustive selection of such patents include 4,680,259, 4,212,938, 4,144,129 and 3,925,164 (cholesterol oxidase); 4,672,029, 4,636,464, 4,490,465 and 4,418,037 (glucose oxidase); and 4,614,714 (L-glutamic acid oxidase). All of these enzymatic systems "oxidize" their substrates (i.e., the analyte in question) in that they remove electrons therefrom.

Once the analyte loses its electrons, it plays no further part in the determination reaction. As indicated, supra, the electrons may be transferred into a color forming systems, such as the Trinder system described in U.S. Pat. No. 4,291,121, or a tetrazolium system, such as is described in, e.g., U.S. Pat. No. 4,576,913. These systems employ substances known as "mediators" "electron transfer agents" or "electron shuttles" which remove the electrons from the enzymes. Eventually, the mediators release the electrons. The mediators can either absorb one, or two electrons per molecule of mediator. Ferricyanide, one preferred mediator, picks up one electron per molecule. The 4,576,913 patent, described supra, e.g., teaches another mediator, i.e., phenazine methosulfate, in combination with a tetrazolium salt. It is the latter which serves as the indicator. The use of these mediators enables one to proceed without oxygen. Normally, in a glucose determination reaction, oxygen is necessary to remove electrons from the reduced enzyme. This produces hydrogen peroxide:

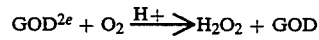

with the hydrogen peroxide taking part, in the presence of peroxidase, in reactions leading to formation of a color.

It is sometimes not desirable to use oxygen, or aerobic systems, because of various problems inherent in such systems. For example, in these reactions, the reaction is dependent on the partial pressure of $O_2$ in the atmosphere. In addition, because the $O_2$ must permeate throughout the entire test medium, the design of such media must be adapted to permit such permeation. There is interest, then, in indicator systems which are anaerobic, such as those where a mediator is used in connection with the indicator, or electrochemical systems using the mediator alone. There exists a need for anaerobic systems which utilize indicator reactions producing a detectable signal, such as a color.

While indicator systems of the type described supra are available, there is a difficulty with these in that the indicator molecules themselves are frequently unstable and do not have long shelf lives. There is therefore an interest in systems which utilize stable molecules which can form a detectable signal.

It will be recalled that Kaplan taught the formation of Prussian Blue in glucose determination, but dismissed it as a viable alternative because of the lack of specificity. Apart from this, the severe conditions under which the reactions are taught to take place are totally unsuitable for enzymatic assays. The reaction Kaplan teaches requires boiling the solutions. Enzymes are protein molecules, and inactivation via denaturing is characteristic of what happens when proteins are boiled. Thus, the skilled artisan, screening the heat parameters of Kaplan would avoid this teaching for enzymatic assays.

Mention of the Prussian Blue system is found in the aforementioned U.S. Pat. No. 4,576,913. This patent teaches a glycerol dehydrogenase which operates in a fashion similar to oxidases in that it teaches removal of two electrons from its substrate molecule. Column 5 of the patent refers to the Prussian Blue system (referred to as "Berlin Blue") as an the indicator.

This patent, however, must be read as a whole, and especially its teaching about the enzyme's operability. Enzymes are extremely pH sensitive, and the enzyme of the '913 patent is said to operate in a pH range from 6.0 to 10.0, and optimally at 7.0 to 8.5. The teachings, therefore, would suggest to the artisan that since the glycerol dehydrogenase operates at alkaline pHs, the adaptation of the Prussian Blue system to enzyme detection would be at alkaline pHs. However, ferric salts precipitate at alkaline pHs, which would eliminate them from participating in a reaction to form Prussian Blue under the conditions Adachi describes as necessary.

Refinements of the Prussian Blue based assay systems are described in U.S. Pat. No. 4,929,545, the disclosure of which is incorporated by reference. This patent teaches that ferrocyanide ions react with ferric ions supplied from the ferric ion containing salt $Fe_3(SO_4)_2$. The system can be used for determination of various analytes, including glucose and cholesterol.

A system similar to the Prussian Blue system is one based upon the chelator ferrozine. U.S. Pat. No. 4,701,420, the disclosure of which is incorporated by reference, describes the reaction. Essentially, the system uses an electron transfer agent together with an NAD(P)H/NAD(P) system. In essence, the reaction involves the transfer of an electron to NAD(P)H from analyte, followed by transfer to the electron transfer agent. In turn, the transfer agent shuttles the electron to a ferric ion containing complex, thereby generating ferrous ions. The ferrous ions then combine with a second material, leading to formation of a colored material. A series of possible materials are described as being useful as complexing agents for the ferric ion. The materials described in the '420 patent are extremely strong chelating agents.

It has now been found, surprisingly, that chelating agents not described as useful in indicator systems and which are weaker chelating agents than these described in the art are much more useful in indicator systems. Thus, these chelating agents are an important part of the invention described herein, which is a novel composition useful for determining analytes. This invention is described in more detail in the disclosure which follows.

SUMMARY OF THE INVENTION

The invention is a composition useful in determining an analyte in a sample. The composition includes, as essential elements, a specific oxidizing agent for the analyte in question, an electron transfer agent, a source of ferric ions, and two chelating agents. The first chelating agent is characterized by an affinity for ferric ions that is greater than its affinity for ferrous ions. The second chelating agent is one which complexes with ferrous ions to form a colored composition indicative of the analyte in question.

The particular of the invention and specific features thereof are set forth in the Detailed Description of Preferred Embodiments which follow.

DETAILED DESCRIPTION OF PREFERRED EMBODIMENTS

Example 1

A well known system for the detection of glucose in a sample involves the following series of reactions:

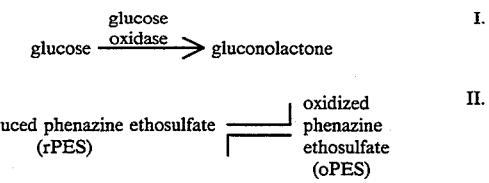

Reactions "I" and "II" are coupled, i.e., in the oxidation of glucose, the electron removed is transferred to oPES, resulting in rPES. This species, rPES, however, immediately shuttles the electron in reaction "III":

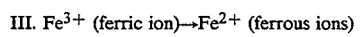

whereby rPES reverts to oPES. The ferrous ion ($Fe^{2+}$) then combines with ferrozine in reaction "IV":

The intensity of purple color is a measurement of glucose.

In this experiment, sodium citrate was used as the chelating agent of the invention. A solution of citric acid (230 mM) was prepared, as was a solution of $Fe_2(SO_4)_3$ (22 mM), and the pH adjusted to 5.00. These species correspond to the chelating agent and the ferric ion of the invention, respectively. A solution of PES (18 mM), i.e., the electron transfer agent, was prepared, as was a solution of glucose oxidase (5 ku/g). Finally, a 60 mM solution of ferrozine was prepared. These materials were combined in a test tube to give a final concentration of 200 mM citric acid, 19.1 mM $Fe_2(SO_4)_3$, 7.8 mM PES, 26.5 mM ferrozine, and 2.5 units of glucose oxidase. A solution of glucose (50 mg/dl) was added to give a final concentration of glucose of 9.1 mg/dl. Color formation was inspected visually, at a wavelength of 563 nm on a spectrophotometer (Shimadzu Model UV160 U), as were reaction kinetics. Absorbance was measured every two seconds over a one minute period.

Example 2

The protocols of Example 1 were followed, except sodium dl malate was used in place of sodium citrate.

Example 3

The protocols of Example 1 were followed, except sodium iminodiacetate was used in place of sodium citrate.

In all three cases, the colorimetric precipitate expected to form (i.e., complexes of ferrous ion and ferrozine) did form, with the citrate mixture forming most rapidly, followed by malate and iminodiacetate being the slowest former. Specifically, a change in absorbance of 1.29 units took 17 seconds for the citrate, 23 seconds for the malate, and 60 seconds for the iminodiacetate. The values are summarized in Tables 1-3, which follows. More color formed with the first two chelating agents than with the iminodiacetate.

TABLE 1

CITRATE

| No. | T (SEC) | ABS | dA |
|---|---|---|---|
| 2 | 0 | 0.409 | |
| | 2 | 0.421 | 0.012 |
| | 4 | 0.426 | 0.005 |
| | 6 | 0.443 | 0.017 |
| | 8 | 0.491 | 0.048 |
| | 10 | 0.658 | 0.167 |
| | 12 | 0.976 | 0.318 |
| | 14 | 1.343 | 0.367 |
| | 16 | 1.678 | 0.335 |
| | 18 | 1.958 | 0.280 |
| | 20 | 2.184 | 0.226 |
| | 22 | 2.362 | 0.179 |
| | 24 | 2.485 | 0.123 |
| | 26 | 2.485 | 0.000 |
| | 28 | 2.485 | 0.000 |
| | 30 | 2.485 | 0.000 |
| | 32 | 2.485 | 0.000 |
| | 34 | 2.485 | 0.000 |
| | 36 | 2.485 | 0.000 |
| | 38 | 2.485 | 0.000 |
| | 40 | 2.485 | 0.000 |
| | 42 | 2.485 | 0.000 |
| | 44 | 2.485 | 0.000 |
| | 46 | 2.485 | 0.000 |
| | 48 | 2.485 | 0.000 |
| | 50 | 2.485 | 0.000 |
| | 52 | 2.485 | 0.000 |
| | 54 | 2.485 | 0.000 |
| | 56 | 2.485 | 0.000 |
| | 58 | 2.485 | 0.000 |
| | 60 | 2.485 | 0.000 |
| LAG T = 0 SEC | RATE T = 60 SEC | | |
| dA/MIN. | ACTIVITY | | |
| 2.4109 | 2.4109 | | |

TABLE 2

MALATE

| No. | T (SEC) | ABS | dA |
|---|---|---|---|
| 3 | 0 | 0.589 | |
| | 2 | 0.602 | 0.013 |
| | 4 | 0.621 | 0.019 |
| | 6 | 0.663 | 0.042 |
| | 8 | 0.766 | 0.104 |
| | 10 | 0.932 | 0.165 |
| | 12 | 1.137 | 0.205 |
| | 14 | 1.342 | 0.205 |
| | 16 | 1.518 | 0.177 |
| | 18 | 1.661 | 0.142 |
| | 20 | 1.769 | 0.108 |
| | 22 | 1.847 | 0.078 |
| | 24 | 1.903 | 0.056 |
| | 26 | 1.942 | 0.039 |
| | 28 | 1.969 | 0.027 |
| | 30 | 1.987 | 0.018 |
| | 32 | 1.999 | 0.012 |
| | 34 | 2.008 | 0.009 |
| | 36 | 2.014 | 0.006 |
| | 38 | 2.018 | 0.005 |
| | 40 | 2.021 | 0.003 |
| | 42 | 2.025 | 0.003 |
| | 44 | 2.027 | 0.002 |
| | 46 | 2.028 | 0.002 |
| | 48 | 2.030 | 0.002 |
| | 50 | 2.031 | 0.001 |
| | 52 | 2.032 | 0.001 |
| | 54 | 2.033 | 0.001 |
| | 56 | 2.034 | 0.001 |
| | 58 | 2.034 | 0.001 |
| | 60 | 2.035 | 0.000 |
| LAG T = 0 SEC | RATE T = 60 SEC | | |
| dA/MIN. | ACTIVITY | | |
| 1.6032 | 1.6032 | | |

TABLE 3

IMINODIACETATE

| No. | T (SEC) | ABS | dA |
|---|---|---|---|
| 1 | 0 | 0.431 | |
| | 2 | 0.443 | 0.012 |
| | 4 | 0.458 | 0.015 |
| | 6 | 0.472 | 0.014 |
| | 8 | 0.487 | 0.015 |
| | 10 | 0.502 | 0.015 |
| | 12 | 0.517 | 0.016 |
| | 14 | 0.533 | 0.016 |
| | 16 | 0.550 | 0.017 |
| | 18 | 0.569 | 0.017 |
| | 20 | 0.588 | 0.020 |
| | 22 | 0.611 | 0.023 |
| | 24 | 0.637 | 0.026 |
| | 26 | 0.672 | 0.035 |
| | 28 | 0.724 | 0.051 |
| | 30 | 0.795 | 0.071 |
| | 32 | 0.880 | 0.086 |
| | 34 | 0.973 | 0.093 |
| | 36 | 1.067 | 0.094 |
| | 38 | 1.158 | 0.091 |
| | 40 | 1.243 | 0.085 |
| | 42 | 1.323 | 0.079 |
| | 44 | 1.395 | 0.072 |
| | 46 | 1.458 | 0.063 |
| | 48 | 1.514 | 0.056 |
| | 50 | 1.562 | 0.048 |
| | 52 | 1.603 | 0.042 |
| | 54 | 1.640 | 0.036 |
| | 56 | 1.671 | 0.031 |
| | 58 | 1.698 | 0.027 |
| | 60 | 1.721 | 0.023 |
| LAG T = 0 SEC | RATE T = 60 SEC | | |
| dA/MIN. | ACTIVITY | | |
| 1.4848 | 1.4848 | | |

The foregoing examples exemplify the use of the reagent compositions useful in determining an analyte in solution. Essential components of the composition include an analyte oxidizing agent, an electron transfer agent, a ferric ion source, a chelating agent which preferentially complexes ions as compared to ferrous ions, and a ferrous ion complexing agent, with the proviso that the chelating agent is not iminodiacetate containing compound.

"Analyte oxidizing agent" as the term is used herein refers to any material which removes an electron from the analyte of interest specifically. Ideally, this is an enzymatic oxidizing agent, as these materials are well known for the specificity of their activity. If glucose is the analyte of interest, for example, glucose oxidase may be used. Similarly, cholesterol oxidase may be used when cholesterol is being determined, and so forth. The art is very familiar with such oxidizing enzymes.

Electron transfer agent, as the term is used herein, refers to a material which accepts the electron from the oxidized analyte, but immediately "shuttles" it to another material. The transfer agents are reusable materials, as the act of transfer occurs very quickly, and in so doing the agent becomes receptive to receipt of further electrons. Non-exclusive examples of electron transfer agents include ferrocyanide compounds, such as potassium ferricyanide, phenazine methosulfate ("PMS"), phenazine ethosulfate ("PES"), and so forth. The electron transfer agent to be used will vary depending upon a number of criteria, including the pH of the composition. For example, potassium ferricyanide may be used at a pH range of from about 3.0 to about 5.5. PES may be used at a much broader range, i.e., at a pH of from about 3.0 to about 9.0. It is noted that the reagent is at a pH greater than about 5.5, however, there is some problem with association of the ferric ion with free hydroxyl groups, leading to formation of insoluble ferric hydroxide. To remedy this potential problem, the chelating agent should be a strong one. A citrate ion based chelator such as citric acid or sodium citrate is preferred for pHs above 5.0. Also preferred are malate containing compounds such as malic acid or sodium malate.

The composition may be prepared in a number of different forms. The examples show solution based materials, however, the compositions may also be formulated as multi part kits. In this case, the elements of the composition may be separated one from another, or different combinations may be prepared. For example, the ferric ion source may be kept in a container apart from the chelating agent, or the two components may be combined in one container. Some or all of the components of the reagent may be in liquid or solid form, such as in aqueous solutions, powders, tablets, lyophilisates, and so forth. The compositions may also be impregnated into an analytical device, such as a test strip or multilayered analytical apparatus. When used in a multilayered device, different components may be incorporated into different layers, so that each of the reactions in the series described supra occurs in a different layer. When a single layer, e.g., a test strip, is used, the reagents may be placed along the strip so that the sequential reactions take place at different points on the strip.

The preceding are examples of types of formulations of the reagent, and are not to be read as limitations thereon.

It will be understood that the specification and examples are illustrative but not limitative of the present invention and that other embodiments within the spirit and scope of the invention will suggest themselves to those skilled in the art.

We claim:

1. Method for determining an analyte in a sample, comprising contacting said sample with a composition which comprises:
    (i) an analyte oxidizing agent,
    (ii) an electron transfer agent,
    (iii) a complex of ferric ions and a chelating agent selected from the group consisting of a citrate ion containing compound, a malate ion containing compound having an affinity for ferric ions greater than its affinity for ferrous ions, with the proviso that an iminodiacetate containing compound is not present, and
    (iv) a ferrous ion complexing agent which forms a color when complexed to ferrous ions, and determining formation of a color in said sample as a determination of said analyte therein.

2. The method of claim 1, wherein said analyte oxidizing agent comprises at least one enzyme.

3. The method of claim 2, wherein said at least one enzyme is glucose oxidase.

4. The method of claim 2, wherein said at least one enzyme is cholesterol oxidase.

5. The method of claim 1, wherein said electron transfer agent is a ferricyanide.

6. The method of claim 1, wherein said electron transfer agent is phenazine ethosulfate.

7. The method of claim 1, wherein said electron transfer agent is phenazine methosulfate.

8. The method of claim 1, wherein said chelating agent is a citrate ion containing a compound.

9. The method of claim 1, wherein said chelating agent is a malate ion containing compound.

10. The method of claim 1, wherein said ferrous ion complexing agent is ferrozine.

11. The method of claim 1, wherein said composition further comprises a buffer.

* * * * *